United States Patent [19]

Luther et al.

[11] Patent Number: 4,832,696

[45] Date of Patent: *May 23, 1989

[54] ASSEMBLY OF NEEDLE AND PROTECTOR

[75] Inventors: Ronald B. Luther, Newport Beach; Pradip V. Choksi, Northridge, both of Calif.

[73] Assignee: Luther Medical Products, Inc., Tustin, Calif.

[*] Notice: The portion of the term of this patent subsequent to Aug. 9, 2005 has been disclaimed.

[21] Appl. No.: 115,407

[22] Filed: Nov. 2, 1987

Related U.S. Application Data

[63] Continuation-in-part of Ser. No. 22,132, Mar. 5, 1987, Pat. No. 4,762,516.

[51] Int. Cl.⁴ ............................................. A61M 5/00
[52] U.S. Cl. .................................. 604/164; 604/168; 604/192; 604/198; 604/110
[58] Field of Search ............................. 604/164–169, 604/158, 162, 263, 192, 198, 110

[56] References Cited

U.S. PATENT DOCUMENTS

| | | | |
|---|---|---|---|
| 3,463,152 | 8/1969 | Sorenson | 128/214.4 |
| 3,536,073 | 10/1970 | Farb | 128/214.4 |
| 4,160,450 | 7/1979 | Doherty | 128/214.4 |
| 4,500,312 | 2/1985 | McFarlane | 604/263 |
| 4,588,398 | 5/1986 | Daugherty et al. | 604/265 |
| 4,631,057 | 12/1986 | Mitchell | 604/198 |
| 4,664,653 | 5/1987 | Sagstetter et al. | 604/197 |
| 4,664,654 | 5/1987 | Strauss | 604/198 |
| 4,676,783 | 6/1987 | Jagger et al. | 604/171 |
| 4,702,738 | 10/1987 | Spencer | 604/198 |

FOREIGN PATENT DOCUMENTS

| | | | |
|---|---|---|---|
| 0139872 | 7/1984 | European Pat. Off. | |
| 0138972 | 8/1985 | European Pat. Off. | 604/168 |

OTHER PUBLICATIONS

"Introducing the ICU High Risk Needle" by ICU Medical, Inc. of 3 pages.

*Primary Examiner*—Dalton L. Truluck
*Assistant Examiner*—Denise Whelton
*Attorney, Agent, or Firm*—Stetina and Brunda

[57] ABSTRACT

An assembly of a needle and a device for protecting the needle tip is disclosed. The assembly comprises an elongate housing which mounts the needle. A needle guard is slidably mounted within the housing and is adapted to be moved forward along the needle. Following use, the needle and housing are retracted and the needle guard becomes permanently locked with the housing while it occludes or covers the needle.

2 Claims, 5 Drawing Sheets

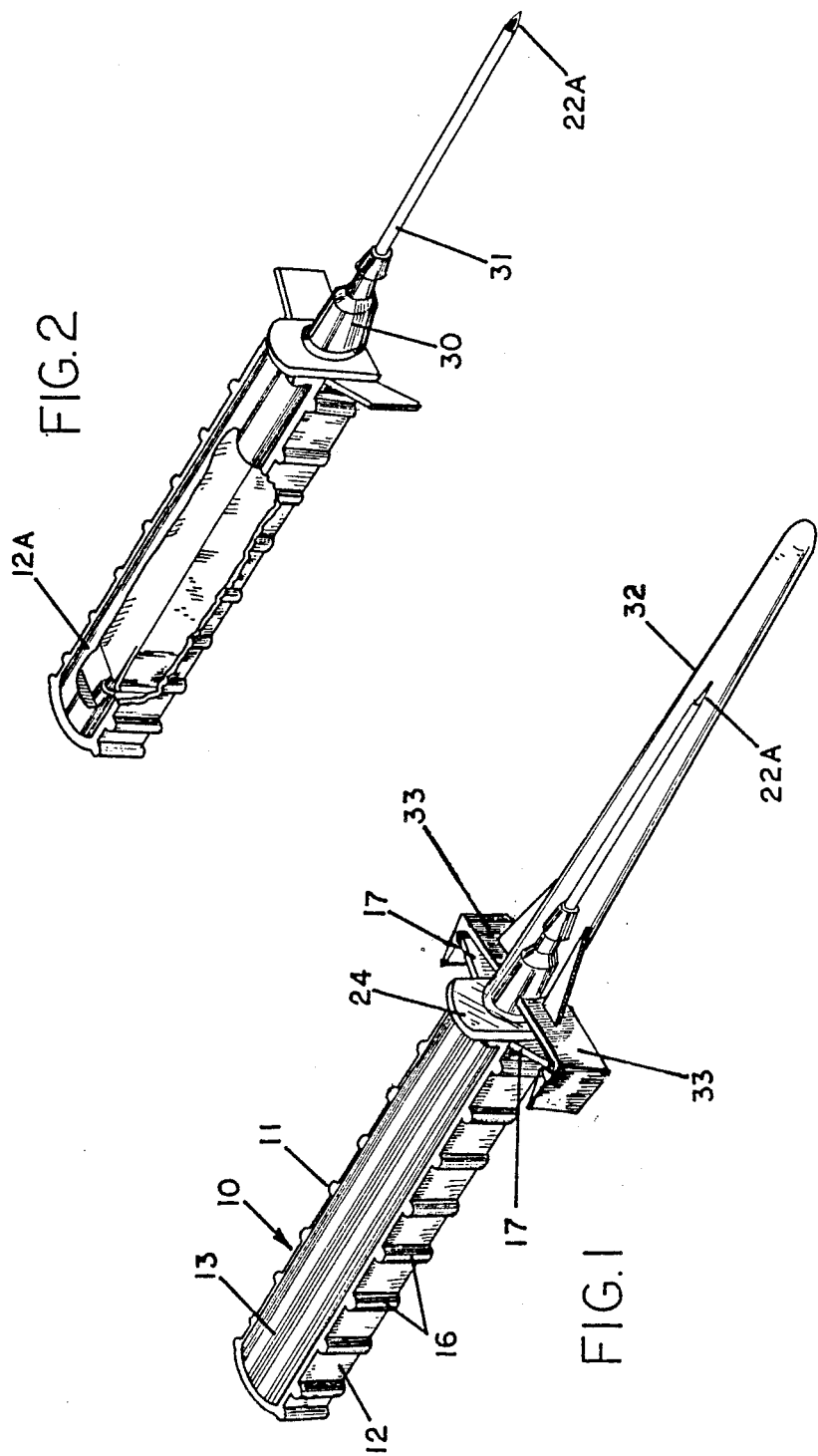

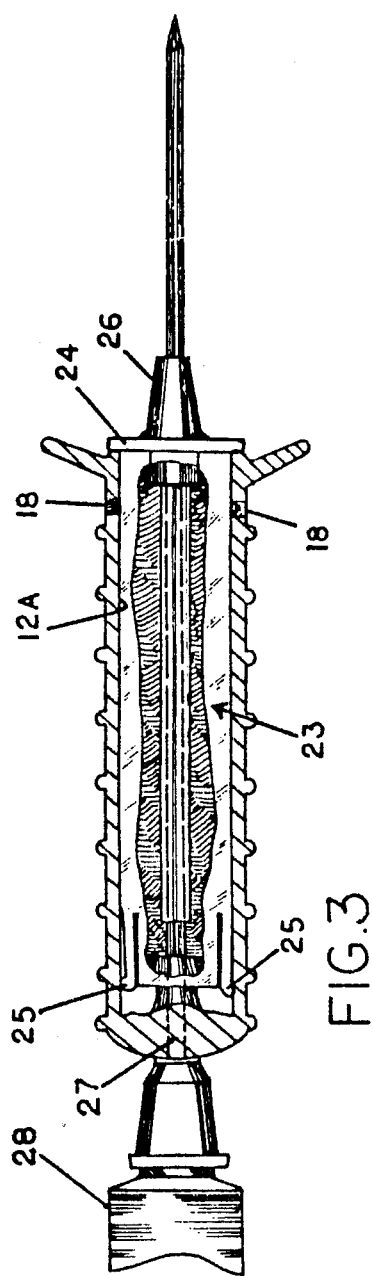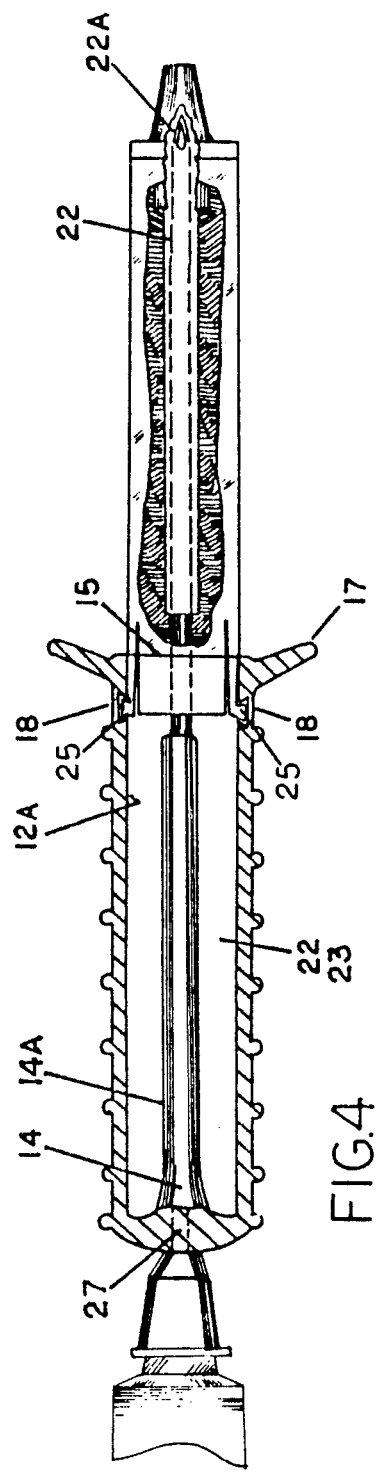

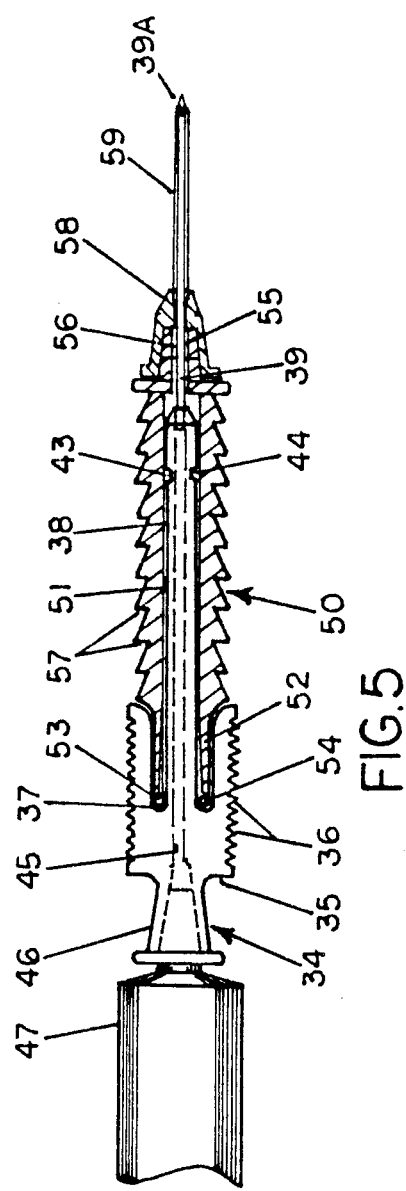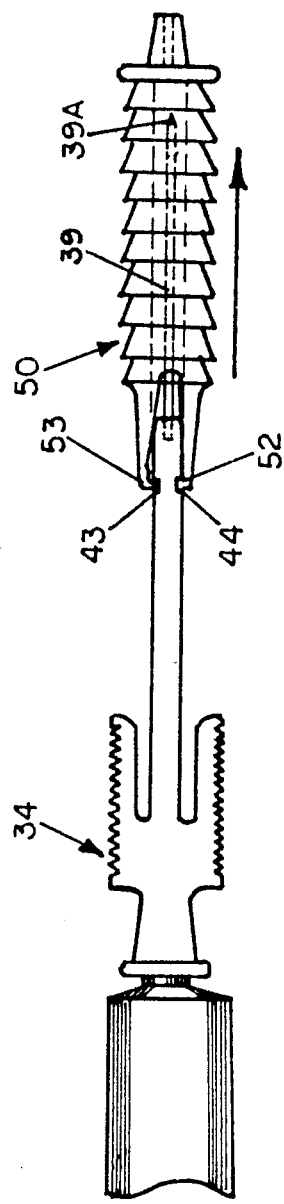

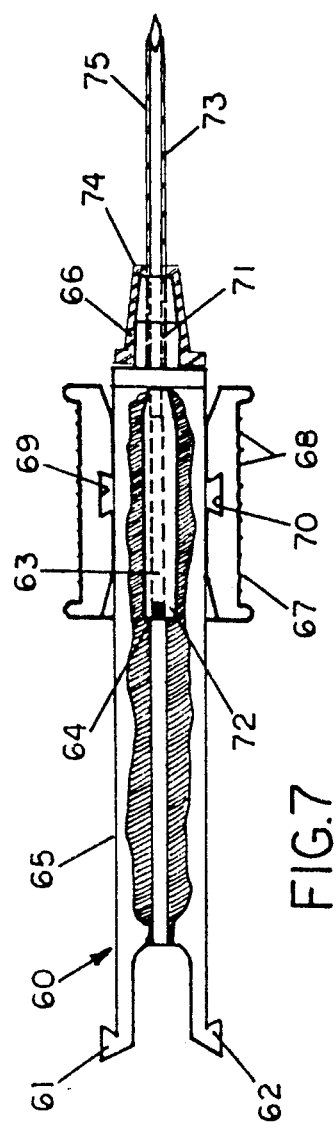
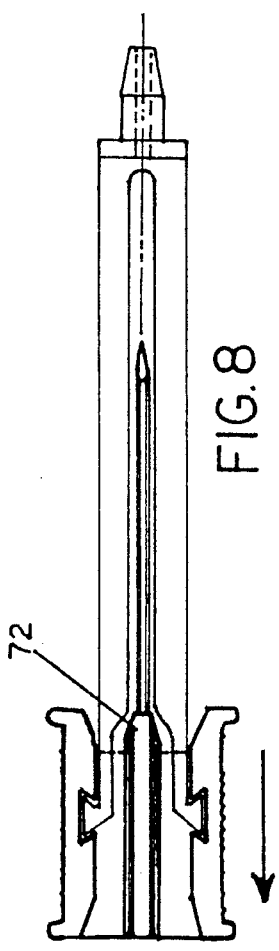
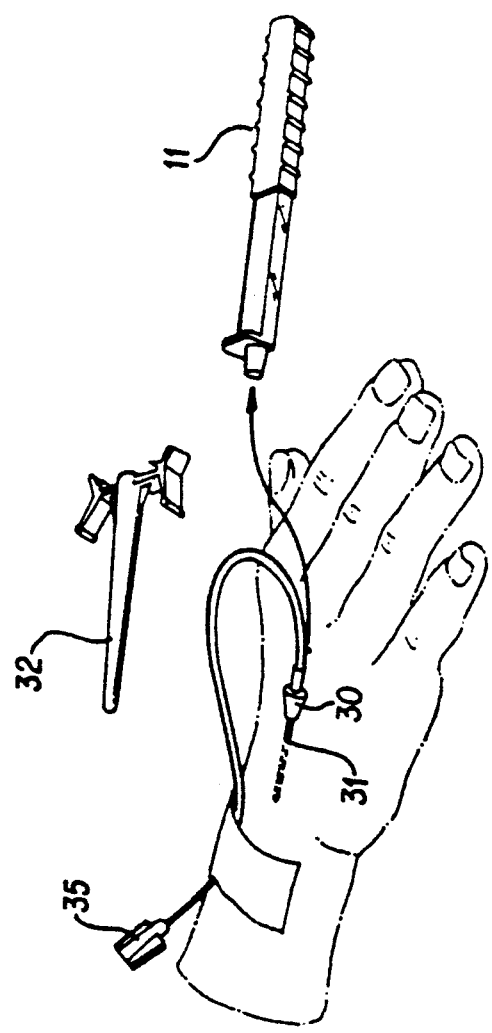
FIG.7
FIG.8
FIG.11

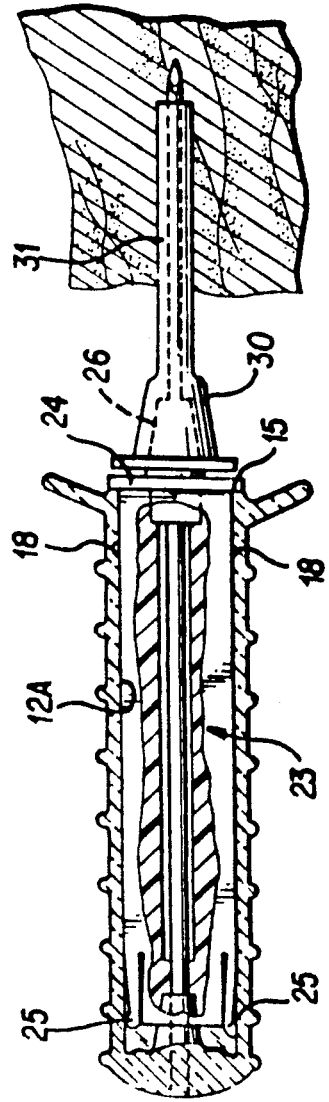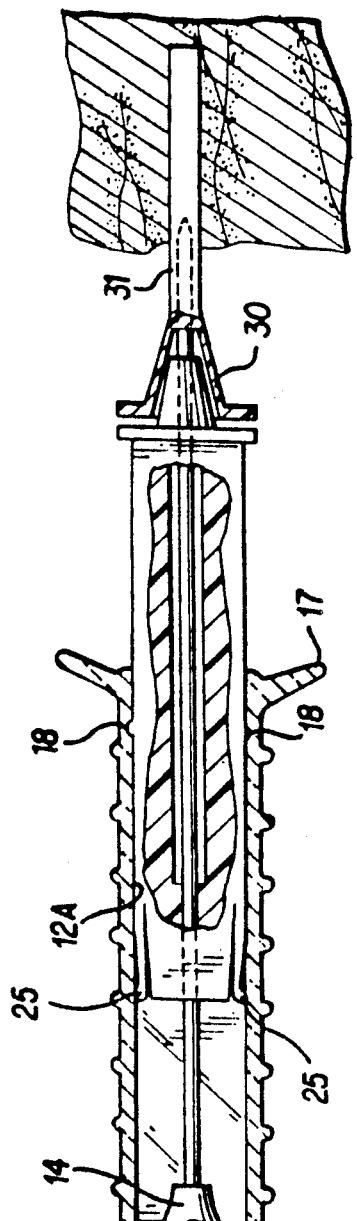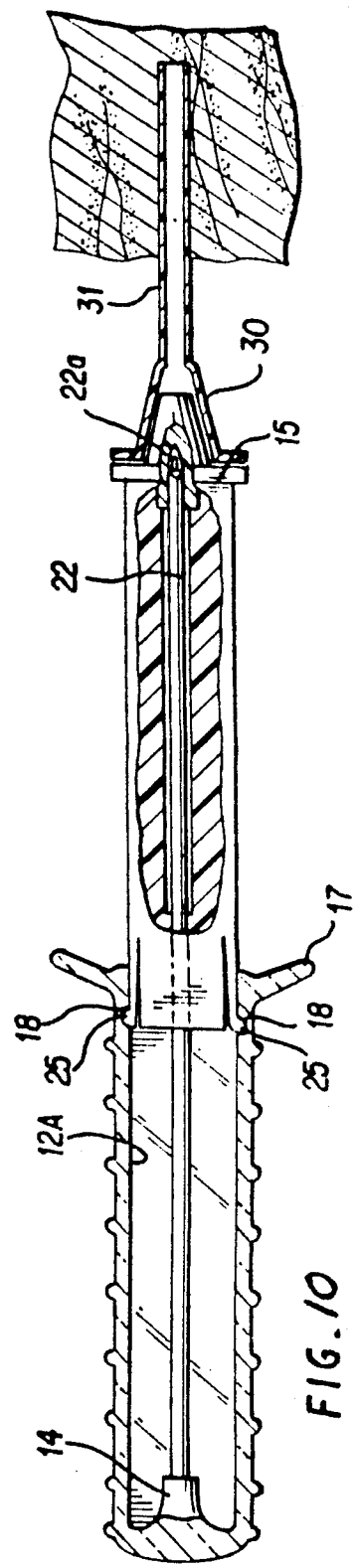

ASSEMBLY OF NEEDLE AND PROTECTOR

BACKGROUND OF THE INVENTION

This application is a continuation-in-part of U.S. Ser. No. 022,132, filed Mar. 5, 1987 which issued as U.S. Pat. No. 4,762,516 on Aug. 9, 1988.

This invention relates to a new and improved assembly of a needle and a protective needle guard therefor.

Following use of a needle, they are usually broken, and discarded to waste. However, there is always a small possiblity that the discarded needle points may inadvertantly stick or scratch medical health personnel. Also, it is desirable that persons who use or come in proximity to used needles will not have to contact them prior to, or subsequent to their use. This is becoming of increasing the importance in reducing accidental infections from patients who have HTLV (AIDS) virus, hepatitis, and other infectious diseases.

There is presently on the market a device sold by ICU Medical which functions to almost completely enclose the needle subsequent to use. However, the device does not provide a housing or protective cover for the needle tip. This, of course, leaves open the possibility of a health care worker being accidentally stuck or scratched.

THE INVENTION

According to the invention, there is provided an assembly of a needle device and needle guard therefor, the needle guard being adapted to slide along the device and completely enclose the needle following use. The needle guard is provided with flexible members which are adapted to lock into the device and prevent the needle guard from being retracted to expose the used needle.

BRIEF DESCRIPTION OF THE DRAWINGS

FIG. 1 is an external, perspective view of the assembled device of this invention;

FIG. 2 is an external, perspective view, partly cutaway, showing the slidable needle guard portion of the assembly;

FIG. 3 is a cross sectional, upper view of the device, with the needle guard in the retracted position, and attached syringe;

FIG. 4 is a cross sectional, upper view showing the needle guard in the extended position covering the needle, and being locked into its associated housing;

FIGS. 5 and 6 are sectional views in side elevation of another embodiment showing a needle support with detent slots and attached needle and hypodermic syringe for engaging detents and a forwardly moveable, associated needle guard;

FIGS. 7 and 8 are sectional views in side elevation of a further embodiment showing a retractable needle support and attached needle, the support providing a handle with detent slots for engaging detent means on an associated needle guard;

FIG. 9 is a cross-sectional view inside elevation of the device, with the needle guard in the retracted position and the needle and catheter being inserted into a patient;

FIG. 9A is a cross-sectional view inside elevation of the device, with the needle being partially retracted from the patient into the needle housing;

FIG. 10 is a cross-sectional view inside elevation showing the needle guard in the extended position covering the needle, and being locked permanently into its associated housing; and FIG. 11 is a an external, perspective view of the device following separation of the hub and catheter from the housing and needle after the catheter has been inserted into a patient.

DESCRIPTION OF THE PREFERRED EMBODIMENTS

The assembly 10 of this invention is shown in FIGS. 1–4, and comprises a rectangular, elongate housing 11 of clear plastic such as injection molded polycarbonate or polystyrene. The clear plastic enables flashback to be readily observed. The housing provides enclosure walls 12 defining inside surfaces 12a, and a magnification portion 13 to better enable viewing blood flashback.

At its closed end, a rear mount 14 with extension 14a inside the housing are adapted to mount and secure a needle. An open end 15 is defined by the housing through which the needle guard moves, and through which the needle projects. Fingergrip ridges 16 are formed on the exterior of the walls, and these also serve to a certain extent to reinforce the housing structure. Stop wings 17 are provided at the open end 15 of the housing along with detent slots 18, the latter being designed to enage the needle guard.

A needle 22 having a bevelled tip 22a is secured within the housing 11 on the extension 14a, the needle projecting through the open end 15 of the housing. A needle guard 23 is slidably mounted within the housing 11, and provides a forwardly located pull tab 24 and outwardly bent locking ears 25. 25. When the needle guard 23 is positioned in the housing 11, the locking ears 25, 25 are biased inwardly by contact with the inside surfaces 12a of the housing walls 12. The biasing is accomplished by using a plastic construction such a polystyrene, polycarbonate, etc., which have flexible properties in a thin wall form. A forward hub support 26 is provided by the needle guard through which the needle 22 projects.

The combined effect of the fixed rear mount 14, extension 14a and forward hub support 26 enables the needle to be maintained stiff and in alignment when it is thrust forward into a patient. Since the extension 14a is manufactured of a plastic material, this represents far less expense than being manufactured of a stainless steel needle material. A rear bore 27 connects the housing 11 with a hypodermic syringe 28.

A luer-type lock hub 30 and catheter 31 are mounted on the hub support 26 with the catheter covering the needle, and only the needle tip 22a being exposed. A cover 32 having wings 33 is usually employed to cover the luer-type lock hub, catheter and needle to reduce loss of sterility and protect the user from the needle 22. The cover 32 is secured to the device by a light interlock with the wings 17 of the housing 11.

When the device is to be used, the cover 32 is removed, as shown in FIG. 2, and the needle 22 and catheter 31 are inserted into a patient as depicted in FIG. 9. With the catheter remaining in the patient as depicted in FIG. 9A, the needle can be withdrawn by pressing against the forward tab 24 while retracting the housing 11 and attached needle 22. Consequently, the needle guard 23 will remain stationary while the locking ears 25, 25 ride along the inside surfaces 12a of the walls 22 of the housing. The locking ears will then snap into their normally outwardly extending configuration (with a clicking sound) and lock into the detent slots 18 of the housing 11. This operation is shown in FIG. 10.

The needle guard is, of course, sized to accommodate the appropriate length of needle within the enclosure of the guard and within the forward hub support 26, as shown in FIG. 4, or within the enclosure of the guard. The hub 30 and attached catheter 31 are shown in FIG. 11 inserted into the patient and connected to an IV unit while the needle 22 and housing 11 are shown separated from the hub, catheter, and patient. Since the needle guard and housing are now permanently engaged, the device can be disposed of without becoming a subsequent source of injury or infection to health care personnel.

It will also be appreciated that when the needle is retracted from the patient, it will pass through the catheter and directly into the needle guard enclosure without any exposure to personnel, and this represents an additional safety feature.

FIGS. 5 and 6 illustrate another embodiment of this invention in which the detent slot means are located on the needle support itself, rather than on the needle housing, and the needle guard provides detent elements which engage the detent slots and lock the guard in place. The needle support 34 provides a handle element 35 having gripping ridges 36 and a circular, internal slot 37 for engaging a needle guard. At its forward end, the needle support 34 provides an elongate, centrally disposed needle mount 38 to which a needle 39 with a needle tip 39a is attached.

Detent slots 43, 44 are defined forwardly of the needle mount 38 and a central bore 45 communicates through a rear hub 46 to the needle 39 for fluid connection with an attached syringe 47. A needle guard 50 for the needle 39 is slidably mounted through its central hollow bore 51 along the needle mount 38 and provides a rear circular portion 52, having detent elements 53, 54 which are biased inwardly by their construction for locking into the detent slots 43, 44 of the needle mount.

The forward end of the needle shield comprises a hub 55 through which the needle passes and which provides a close fitting bore 56 to ensure needle rigidity when in use. The exterior of the needle shield 50 defines a plurality of gripping ridges 57. A catheter hub 58, bearing a catheter 59 are mounted on the hub 55, with the needle tip 39a projecting through the catheter.

In the retracted position shown in FIG. 5, the rear circular portion 52 of the needle guard 50 fits into the internal slot 37 formed between the handle element 35 and the needle mount 38, and remains stationary therein when the needle and catheter are thrust into the patient. As shown in FIG. 6, when the needle is removed from the patient following verification of vein location, the needle guard 50 is advanced so that the detent elements 53, 54 are biased inwardly and lock into the detent slots 43, 44. The needle 39 is totally recessed within the needle guard 50, and hence will not cause accidental needle sticks following use; the used device can then be safely discarded. Also, it is extremely difficult to reuse the device, and this considerably reduces the possibility of infection.

FIGS. 7 and 8 illustrate another embodiment of this invention, and show a needle guard 60 providing outwardly biased, rear locking elements 61, 62 and a hollow bore 63 in fluid connection with a needle. A hydrophobic plug 64 prevents blood flow beyond the bore 63. The exterior of the needle guard 60 defines a longitudinal side wall 65 which terminates in a catheter mount 66 having a bore 71; a catheter hub 74 and attached catheter 75 are mounted thereon.

A handle 67 defining gripping ridges 68 on its exterior surface is mounted for movement on the side wall 65. The needle handle defines slot elements 69, 70 which are adapted to engage the rear locking elements 61, 62 of the needle guard 60. The needle handle 67 provides a hollow centrally disposed needle support member 72 on which a needle 73 is mounted.

When the needle handle is in the forward position, as shown in FIG. 7, the needle 73 projects through the bore 71 of the hub 66, making a close fit therewith; this provides a good support for the needle. After needle puncture, and needle withdrawal from the patient, the needle handle 67 and attached needle 73 are retracted along the needle guard until the outward biasing of the rear locking elements 61, 62 of the needle guard engage the slot elements 69, 70 thereby locking and recessing the needle well within the needle guard. The catheter hub 74 and catheter 75 remain with the patient for connection to, say, an I.V. unit.

A wide range of needle sizes are usefully utilized in the assembly, the range from about 12–26 gauge. Also, many types of catheters may be used insofar as materials are concerned, such as expandable, hydrophilic polymers, TEFLON, PVC nylon, polyurethane, etc., which are all available.

We claim:

1. An assembly of a needle and protector therefor, comprising:
   a. an elongate housing having sidewalls, and a first part of a detent means defined thereon;
   b. a needle connected to the housing and projecting outwardly beyond one end of said housing;
   c. a needle guard slidably connecting with the housing, the needle guard having a pull tab at its forward end, and including a second part of said detent means, the needle guard providing at its forward end a hub support defining a bore therein;
   d. a luer-type hub and catheter mounted on the hub support, the needle being aligned within the hub support, hub and catheter, and projecting through the catheter to expose a tip thereof;
   e. whereby,
      i. following insertion of the needle and catheter into a patient, the housing and attached needle are adapted to be retracted from the patient, and the needle is adapted to be retracted into the needle guard thereby enabling the sidewalls of the housing to slide in relation to the needle guard until the first and second parts of the detent means are aligned and lock together, the needle guard being sized to completely enclose the needle upon locking with the housing;
      ii. the hub and catheter remain with the patient;
      iii. the housing and enclosed needle are separated from the hub, catheter and patient.

2. An assembly of a needle and protector therefor, comprising:
   a. an elongate housing providing sidewalls, and detent means defined thereon, the housing having a first end and a second end;
   b. a needle mounted to the housing and projecting through said first end of the housing;
   c. a needle guard slidably mounted to the housing, the needle guard having a pull tab at its forward end, and biased ears at least partially in contact with the sidewalls of the housing, the needle guard providing at its forward end a hub support defining a bore therein;

d. a luer-type hub and catheter mounted on the hub support, said needle being aligned within the hub support, hub and catheter, and projecting through the catheter to expose a tip thereof;

e. whereby,
   i. following insertion of the needle and catheter into a patient, the housing and attached needle are adapted to be retracted from the patient, and the needle is adapted to be retracted into the needle guard thereby enabling the walls of the housing to slide relative the biased ears of the needle guard, the ears projecting into the detent means of the housing and permanently locking therewith, the needle guard being sized to completely enclose the needle upon locking with the housing;
   ii. the hub and catheter remain with the patient; and
   iii. the housing and enclosed needle are separated from the hub, catheter and patient.

* * * * *